United States Patent [19]

Meserol

[11] Patent Number: 4,577,970
[45] Date of Patent: Mar. 25, 1986

[54] CUVETTE WITH INTEGRAL OPTICAL ELEMENTS

[75] Inventor: Peter M. Meserol, Montville, N.J.

[73] Assignee: Personal Diagnostics, Inc., Whippany, N.J.

[21] Appl. No.: 512,119

[22] Filed: Jul. 8, 1983

[51] Int. Cl.⁴ ............................................. G01N 21/00
[52] U.S. Cl. .................................... 356/440; 356/246; 356/436
[58] Field of Search ......................... 356/246, 440, 436

[56] References Cited

U.S. PATENT DOCUMENTS 3,861,809  1/1975  Hall .................................. 356/246 X Primary Examiner—Bernard D. Pianalto
Attorney, Agent, or Firm—R. Gale Rhodes, Jr.

[57] ABSTRACT

A cuvette provided with integral optical elements for use in photometric measurements, wherein the cuvette includes means, such as a cell, for receiving a medium, such as a seeded culture growth medium, undergoing change in optical characteristics which change modifies the energy level of a ray of energy, such as a transilluminating ray of light, passing through the medium, and wherein the cuvette is further provided with integrally formed first and second ray modifying optical means, such as integrally formed collimating and collecting lens, wherein the first ray modifying means receives and modifies the ray in a first predetermined manner, such as by collimation, and transmits the ray into the medium and wherein the second ray modifying optical means receives and modifies the ray in a second manner, such as by collection, upon the ray passing through the medium and transmits the ray from the cuvette.

15 Claims, 20 Drawing Figures

FIG. 4
FIG. 5
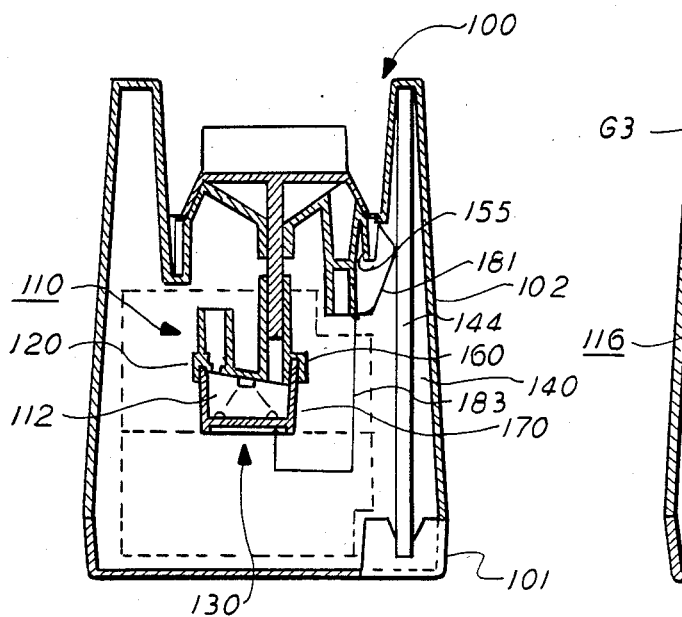
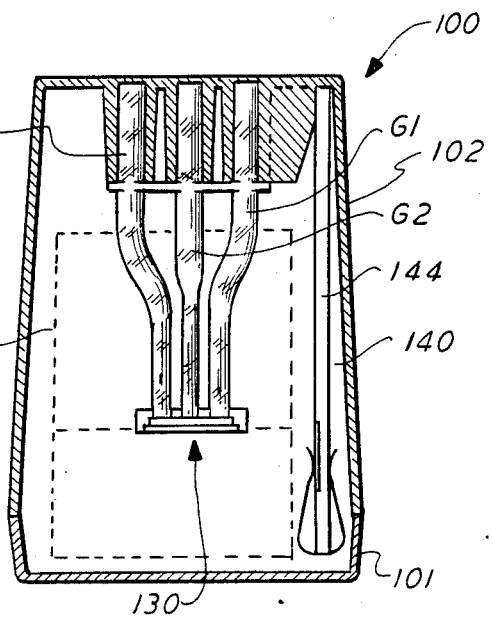
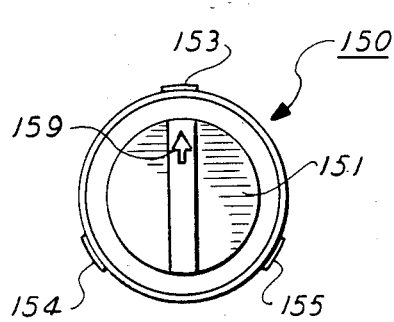
FIG. 6
FIG. 7
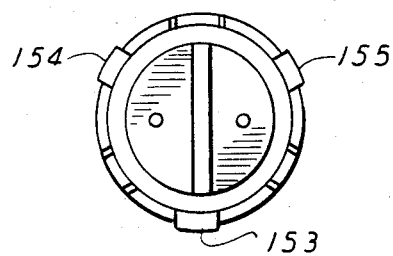
FIG. 8

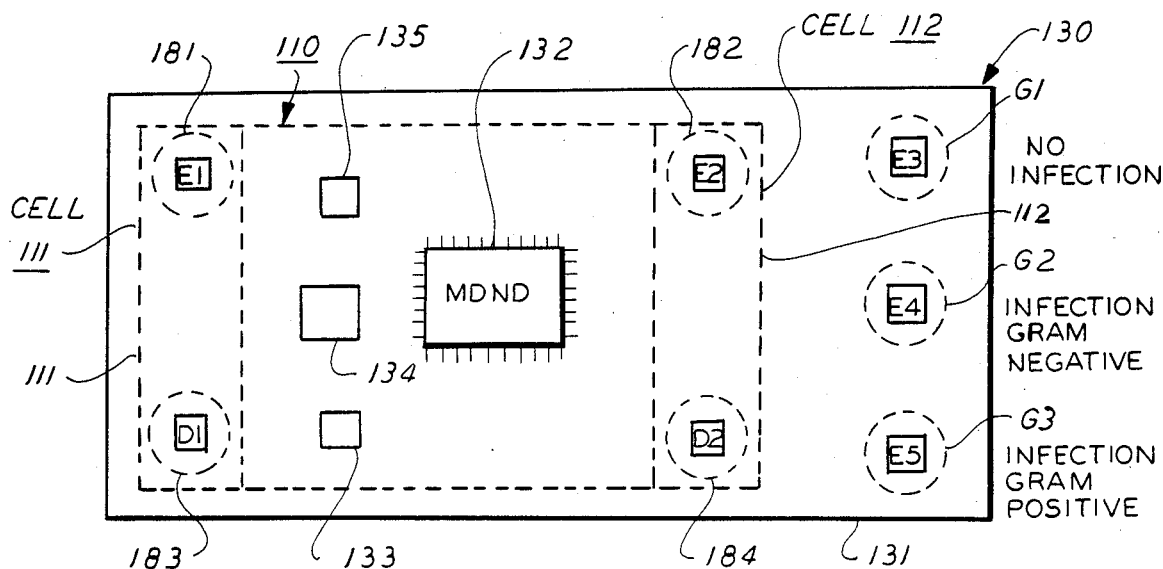
FIG. 10
FIG. 11
DECODER ALGORITHM
1=CLINICALLY SIGNIFICANT GROWTH
0=NO CLINICALLY SIGNIFICANT GROWTH
| CUVETTE CELL 111 (G+) | 1 | 0 | 0 | 1 |
|---|---|---|---|---|
| CUVETTE CELL 112 (G−, OR G− AND G+) | 0 | 1 | 0 | 1 |
| OUTPUT LIGHTS | G+ | G− | NO INFECTION | G+ |
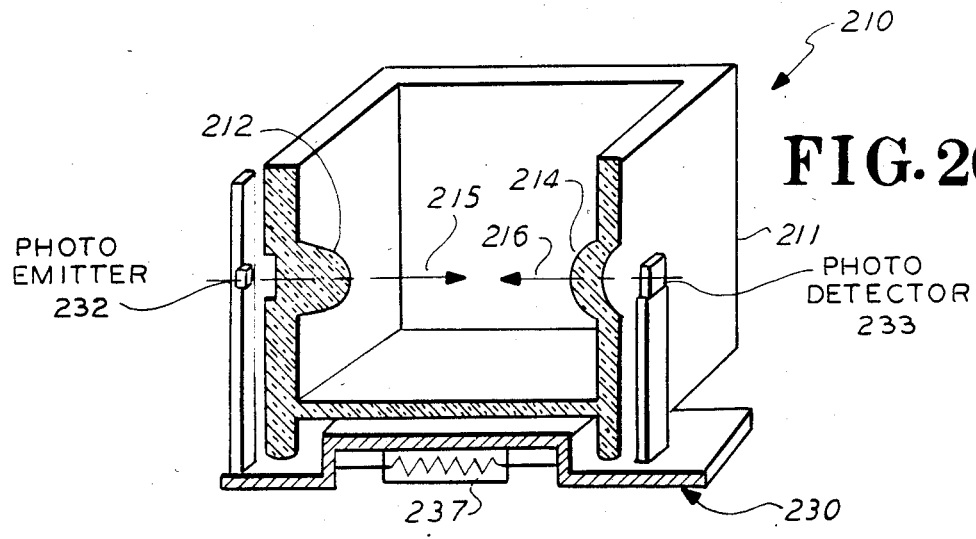
FIG. 20

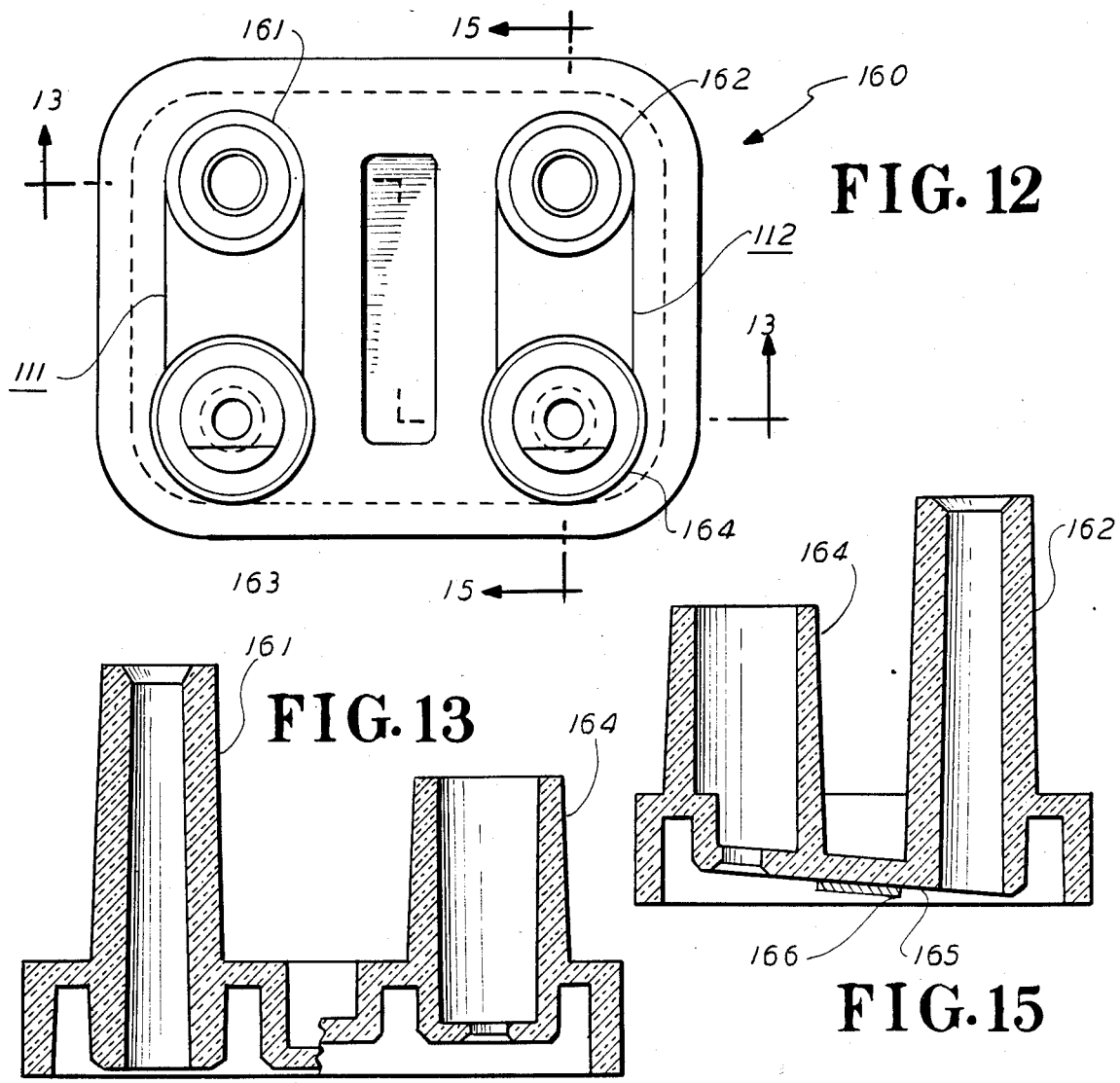
FIG. 12
FIG. 13
FIG. 15
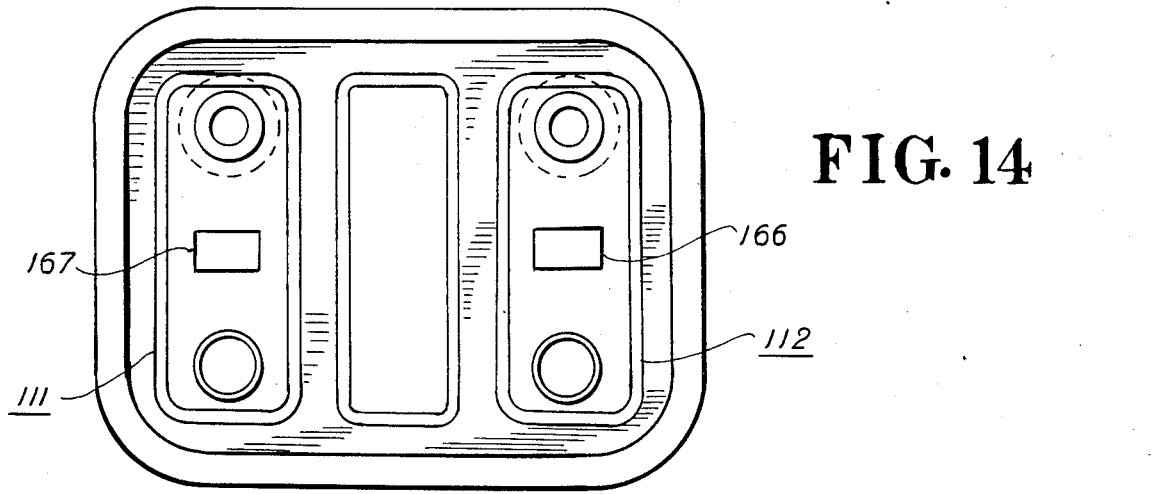
FIG. 14

4,577,970

CUVETTE WITH INTEGRAL OPTICAL ELEMENTS

FIELD OF THE INVENTION

This invention relates generally to the field of cuvettes and more particularly to a cuvette with integral optical elements, such as for example, collimating and collecting lens.

BACKGROUND OF THE INVENTION

The determination of characteristics of chemical or microbiological reactions in in vitro techniques has been characterized by the utilization of plain sided optical cuvettes known to the prior art. These cuvettes, generally, operating in cooperation with laboratory instruments such as spectrophotometers or fluorometers, have sides, bottoms, or caps designed so as not to interact with an analytic beam of light transmitted through them. Examples of such prior art cuvettes are disclosed in U.S. Pat. No. 3,718,439 issued Feb. 27, 1973 to Rosse, U.S. Pat. No. 3,744,975 issued July 10, 1973 to Mailen, U.S. Pat. No. 4,066,414 issued Jan. 3, 1978 to Selby and U.S. Pat. No. 4,083,638 issued Apr. 11, 1978 to Sandrock et al.

In situations where an intimate optical relationship of the analytic device and the cuvette is necessary or desirable to enhance the efficiency or cost of such a device, it is helpful to have molded within the cuvette itself certain members of the optical components which act in cooperation with the device in which the cuvette is placed.

Accordingly, it is the object of the present invention to provide a cuvette with integral optical elements, such as for example collimating and collecting lens, whereby the cuvette may be more efficiently and inexpensively optically coupled to the analytical devices or instruments with which they are used.

SUMMARY OF THE INVENTION

The foregoing object is satisfied by the cuvette of the present invention provided with integral optical elements for use in photometric measurements, wherein the cuvette includes means, such as a cell, for receiving a medium, such as a seeded culture growth medium, undergoing change in optical characteristics which change modifies the energy level of a ray of energy, such as a transilluminating ray of light, passing through the medium, and wherein the cuvette is further provided with integrally formed first and second ray modifying optical means, such as integrally formed collimating and collecting lens, wherein the first ray modifying optical means receives and modifies the ray in a first manner such as by collimation and transmits the ray into the medium and wherein the second ray modifying optical means receives and modifies the ray in a second manner, such as by collection, upon the ray passing through the medium and transmits the ray from the cuvette.

BRIEF DESCRIPTION OF THE DRAWINGS

A better understanding of the present invention as well as other objects and advantages thereof will become apparent upon consideration of the detailed disclosure thereof, especially when taken with accompanying drawings, in which like numerals indicate like parts throughout, and wherein:

FIG. 4 is a cross-sectional view taken along the line 4—4 of FIG. 1;

FIG. 5 is a cross-sectional view taken along the line 5—5 of FIG. 1;

FIGS. 6, 7 and 8 are, respectively, plan, side and bottom views of an incubator cap;

FIG. 10 is a diagrammatical illustration of the electrical circuitry or hybrid circuit;

FIG. 11 is a truth table showing the decoder algorithm used in the incubation assembly;

FIG. 12 is a plan view of the top of a transparent cuvette;

FIG. 13 is an irregular cross-sectional view taken along the line 13—13 of FIG. 12;

FIG. 14 is a bottom view of the transparent cuvette of FIG. 12;

FIG. 15 is a cross-sectional view taken along the line 15—15 of FIG. 12;

FIG. 20 is a partial cross-sectional view of an alternate embodiment of the present invention.

DETAILED DESCRIPTION OF THE INVENTION

To satisfy the requirements of 35 U.S.C. 101, that to be patentable an invention must be useful, the cuvette with integral optical elements of the present invention will be taught as being useful in a self-sufficient incubation assembly; however, it will be undertood that the present invention is not so limited and that the present invention is limited only by the scope of the claims and the prior art.

Referring now to FIGS. 1 to 12, there is illustrated a self-sufficient incubation assembly in which the present invention is useful, the incubation assembly is embodied in the manner taught in detail below, as a self-sufficient urinary tract infection kit for indicating the presence of a Gram negative infection, a Gram positive infection, or the absence of both.

Figure 1:
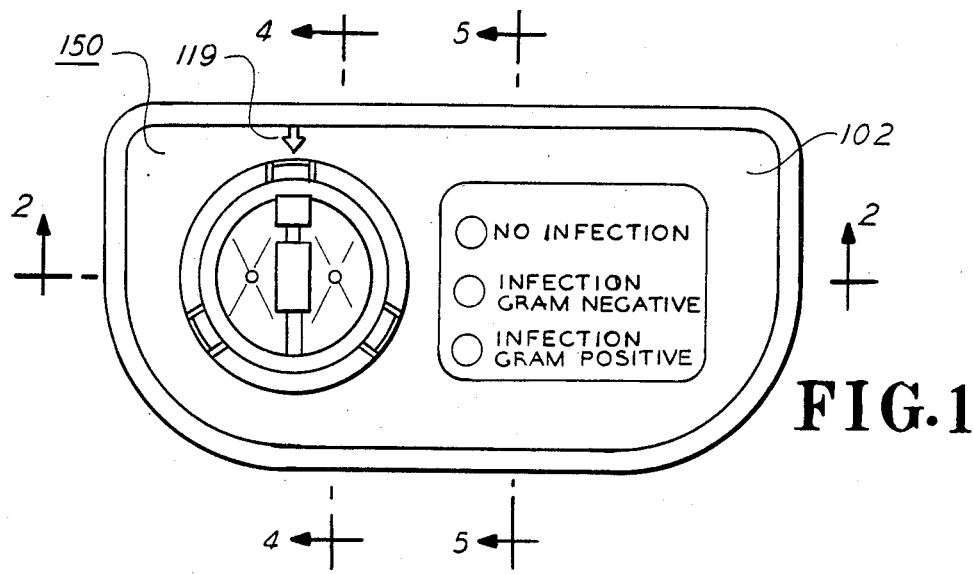
FIG. 1 is a plan view of a self-sufficient incubation assembly in which the present invention may be used.

Referring now specifically to FIGS. 1–5, and initially to FIG. 1, the self-sufficient incubation assembly is indicated by general numerical designation 100. The assembly includes a bottom 101 and a top 102, which are essentially shell-like structures, assembled together and provided with required structural rigidity by telescopically interconnecting posts 103 and 104, and posts 105 and 106; posts 103 and 104 being best seen in FIG. 2 and posts 105 and 106 being shown only in FIG. 3 for clarity of illustration. The assembly 100 further includes a transparent cuvette 110 providing a first cell 111 and a second cell 112, each cell for receiving a portion of a seeded liquid culture growth medium such as eugonic broth seeded with a urine sample from a urinary tract suspected of having a urinary tract infection such as a Gram negative or Gram positive infection.

Figure 2:
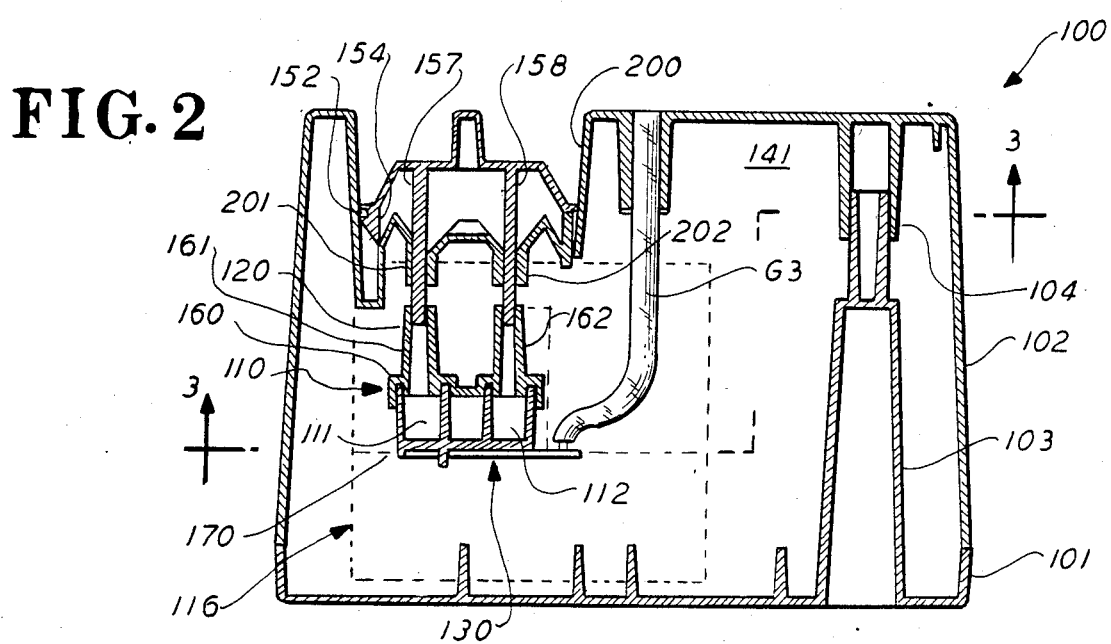
FIG. 2 is a cross-sectional view taken along the line 2—2 of FIG. 1.
Figure 3:
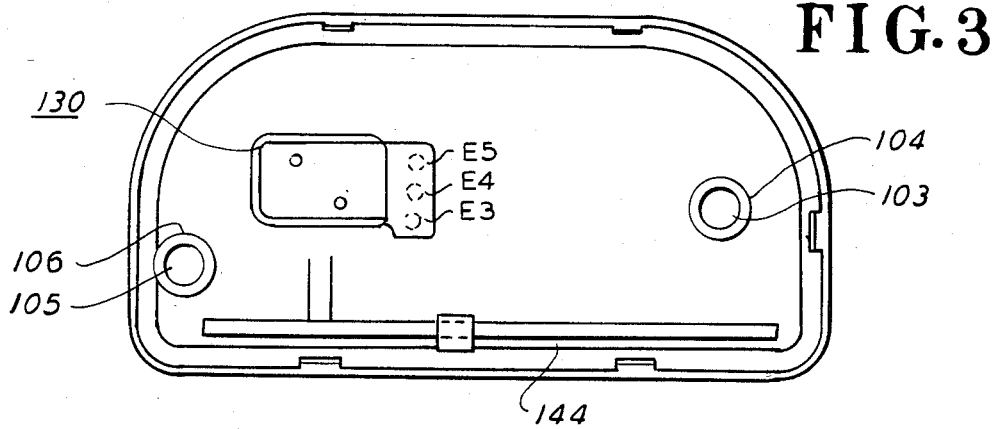
FIG. 3 is an irregular cross-sectional view taken along the line 3—3 of FIG. 2.

The assembly 100 further includes an insulator, of suitable material, indicated by general numerical designation 116 and the two blocks shown in dashed outline in FIGS. 2, 4, and 5; the insulator 116 provides a chamber 120 for receiving the transparent cuvette 110 and insulates the cuvette and seeded liquid culture growth medium received therein during cultivation or incubation. It will be understood that for desired insulation the walls of the chamber 120 for receiving the cuvette 110 must be complementary to the external configuration of the cuvette and such is the case in the assembly, and hence it will be understood that the chamber 120 is coincident with the line defining the exterior of the cuvette and hence no physically distinct chamber 120 is shown. Further, it will be understood that since the cuvette 110 is of irregular configuration, the insulator 116 is made in two pieces, suitably shaped and assembled together, to provide the intimate contact between the insulator and the cuvette for desired insulation.

Electrical circuitry, as indicated by general numerical designation 130, is included and, is in intimate physical contact with the under side of the transparent cuvette 110 to provide intimate thermal and optical contact between the electrical circuitry and cuvette. The electrical circuitry 130, as may be best understood from the diagrammatical illustration of FIG. 10, may include a monolithic chip 132, a film heating resistor 133 for heating the cuvette 110 and seeded culture growth medium received therein to a physiological temperature for the cultivation of microorganisms such as bacteria, a film temperature calibrating resistor 134, a temperature sensing element such as thermistor chip 135 for controlling the heat resistor 133 and thereby controlling to the desired physiological temperature the heat applied to the cuvette and the seeded culture growth medium received therein, a first photoemitter and photodetector pair E1 and D1, a second photoemitter and photodetector pair E2 and D2, and additional photoemitters E3, E4 and E5. For example, the substrate 131 may be of a melamine fiberglass base, a porcelainized metal base, or a ceramic substrate. The photoemitters and photodetectors may be suitable available emitter and detector dies suitably bonded to the substrate at appropriate locations as shown; the film resistors may be suitably available such resistors and also suitably deposited on the substrate at appropriate locations as shown; the thermistor chip 135 may be a suitable available semiconductor thermistor chip suitably bonded to the substrate as shown; and the monolithic chip 132 may be made of any one of several methods known to the prior art and may be made to embody, in combination with the pairs of photoemitters and photodetectors E1 and D1 and E2 and D2, a photometer, such as a turbidity meter, and further embody circuitry for baselining the photometer, temperature monitoring of the cuvette, indicator light illumination of the photoemitters E3, E4 and E5, as well as temperature control of the seeded culture growth medium during cultivation or incubation of the microorganisms or bacteria. The monolithic chip 132 also may be suitably bonded to the substrate 131 and interconnected to the other electrical elements via bonding wires in the manner well known to those skilled in the art.

The assembly 100 also includes an optical system for providing an external indication of the growth of the microorganisms or bacteria within the closed interior of the self-sufficient incubation assembly. This may be best understood by reference to FIGS. 5 and 10, where three electro-optical guides G1, G2 and G3 are shown in physical and electro-optical registration and communication with the photoemitters E3, E4 and E5, respectively, and communicate illumination emanating from these photoemitters to the exterior of the assembly to provide an external visual indication of the detection of growth of microorganisms or bacteria deep within the closed exterior of the assembly. The electro-optical light guides G1, G2 and G3 may be supported and positioned, for example, by suitable complementary shaped guideways formed in the insulator 16.

Referring now more specifically to the structure of the transparent cuvette 110, as may be noted generally from reference to FIGS. 2 and 4, the cuvette is comprised of a top 160 and a bottom 170 each made of suitable transparent material, such as a suitable transparent moldable plastic, and adhered together by a suitable adhesive or bonding operation; the irregular configuration and closed container aspect of the cuvette 160 require, for cost and convenience of manufacture, that it be made in two pieces, namely the top 160 and bottom 170, and thereafter assembled. Referring specifically to FIGS. 12-15 and the specific structure of the cuvette top 160, it will be noted that the top is provided with a pair of upwardly extending intake or entrance galleries 161 and 162 and a pair of shorter and upwardly extending exiting or venting galleries 163 and 164. It will be understood that entrance gallery and venting gallery 161 and 163 are associated with cuvette cell 111 and that entrance gallery 162 and venting gallery 164 are associated with cuvette cell 112; hence, the entrance gallery 161 and venting galery 163 operate as a pair and the entrance gallery 162 and venting gallery 164 operate as a pair. As may be best understood by reference to FIG. 15, and with regard to cell 112, the upper surface of the cell, provided by the lower surface 165 of the top 160, is inclined or angled to insure venting upon filling of the cell with a seeded culture growth liquid medium and in a manner explained in detail later, reflector 166, such as a strip of shiny metal or tape or other suitable surface treatment, is suitably adhered to the top 165 to reflect light from the photoemitter E2 to the photodetector D2; it will be understood that cell 111 is also provided with an inclined top and a reflector 167 as shown in FIG. 14; the reflector 167 is for reflecting light from the photoemitter E1 to the photodetector D1.

The cuvette bottom 170, as shown in detail in FIGS. 14-19, is provided with a plurality of integrally formed, upwardly extending walls 171-176 defining cuvette cells 111-112 and the space 113 therebetween. The bottom 170 further includes upwardly extending integrally formed meniscus collimating lens 181 and 182 and integrally formed meniscus collecting lens 183 and 184. It will be understood that the collimating lens 181 and collecting lens 183 are associated with cuvette cell 111 and hence operate as a pair and that collimating lens 182 and collecting lens 184 are associated with cuvette cell 112 and hence operate as a pair; it will be still further understood that collimating lens 181 and collecting lens 183 operate or function in cooperation with reflector 167 and that collimating lens 182 and collecting lens 184 operate or function in cooperation with reflector 166 as shown in FIG. 25. As is further shown in FIG. 19, the respective axes of the collimating and collecting lens 182 and 184 are disposed at suitable angles with respect to the reflector 166 (shown in dashed outline but shown where the reflector 166 is positioned upon assembly of the cuvette top and bottom) such that a beam or ray of light collected by lens 182 from photoemitter E2 is focused on the reflector 166 and the reflector reflects the received light along the axis of the collimating lens 184 to the photodetector D2, similarly with regard to collimating and collecting lens 181 and 183, reflector 167 and photoemitter E1 and photodetector D1. The bottom 170 is provided with locating pins 188-189 to establish proper registration of the cuvette 110 with the electrical circuitry 130.

The self-sufficient incubation assembly may also be provided with a cap indicated by general numerical designation 150 and which cap is shown in detail in FIGS. 6 and 8. Generally, cap 150 has a dual function, namely it seals or closes the cuvette 110 upon a seeded liquid culture growth medium being received therein for microorganism cultivation and also interconnects the electrical circuitry 130 with the battery 144. Specifically, and referring to FIGS. 6-8, the cap includes a top 151, a plurality of radially disposed and downwardly extending members 153, 154 and 155 for being received in correspondingly radially disposed and downwardly extending slots formed in the top 102 of the assembly 100 as may be best seen in the upper lefthand portion of FIG. 8. Additionally, the cap 150 is provided with a pair of downwardly extending plug members 157 and 158 for respectively entering and sealing the entrance galleries 161 and 162 as is also shown in FIG. 2. It will be further understood that the cap 150 has two positions, the first position with the arrow 159 of the cap (FIG. 6) not aligned with the arrow 119 provided on the top of the assembly as shown in FIG. 1 and in this position the cap does not interconnect the electrical circuitry 130 with the battery 144 and the cap is not locked to the assembly 100. However, upon the seeded liquid culture medium being placed in the cuvette 110 and operation of the assembly being desired, the cap is rotated 180° to align the arrows 159 and 119 and the cap is inserted into the top portion of the assembly whereupon the plug members 157 and 158 seal the entrance galleries 161 and 162 and the downwardly extending member 154, as shown in FIG. 2, is provided with an inwardly extending slot or groove which is engaged by the outwardly extending resilient member 152, as shown, to lock the cap 150 to the top 102 of the assembly 100 to close and seal the assembly for incubation. Additionally, upon the arrows 159 and 119 being aligned and the cap inserted into the top of the assembly, the downwardly extending member 155, as may be best seen in FIG. 4, engages a spring mounted electrical connector 181 to force the connector into engagement with the battery 144 to interconnect the battery 144 through the electrical connector 183 to the electrical circuitry 130 to energize the circuit and commence incubation.

Referring again to FIG. 2, and to the upper lefthand portion, it will be understood that the top 112 is formed inwardly to provide a receptacle 200 which is provided at its bottom with an integrally molded pair of funnels 201 and 202 aligned vertically with the entrance galleries 161 and 162 of the cuvette 110.

The operation of the self-sufficient incubation assembly 100, and the present invention will now be described for use as a urinary tract infection kit although it will be understood by those skilled in the art that the present invention is not so limited but is of general use. As is further known to those skilled in the art, bacteria can be classified into two groups, Gram negative and Gram positive bacteria. As is further known to those skilled in the art, urinary tract infection is caused primarily by Gram negative bacteria such as Ecoli; however, as is also known, urinary tract infection can be caused by Gram positive bacteria. While virtually all sampled urine contains some bacteria, the levels of bacteria of concern are those levels which are referred to in the art as clinically relevant levels of bacteria, for example, 100,000 bacteria per ml, and it is the early detection of the presence of such clinically significant levels of bacteria that is the purpose of urinary tract infection detection apparatus in order that appropriate antibiotics can be prescribed and taken before the onset of a virulent bacterial infection.

As is further known to those skilled in the art, Gram negative bacteria reproduce faster than Gram positive bacteria, Gram negative bacteria reproducing approximately every 20 minutes while Gram positive bacteria reproduce approximately every 40 minutes, that is at approximately one half the rate of Gram negative bacteria. Hence, with this reproduction information, bacteria in a urine sample from a urinary tract suspected of having an infection may be cultivated at a physiological temperature, such as for example 37° C. or 98.6° F., for a given period of time such as for example approximately four hours, and the bacteria level present at the beginning of the period per ml may be compared with the bacteria present per ml at the end of the period and the presence or absence of a clinically significant level of bacteria can be determined. In addition, by knowing the respective reproduction rates of Gram negative and Gram positive bacteria, and by comparing the respective growths of such bacteria over the time interval, the logical determination of the presence of a Gram negative infection or of a Gram positive infection can also be determined or clinically inferred.

As is further known to those skilled in the art, the growth of bacteria in a sample, such as a seeded liquid culture growth medium, over a given period of time can be determined or measured by the use of a photometer such as a turbidity meter. At the beginning of the time interval, the optical density of the sample can be measured by passing a transilluminating beam or ray of light through the sample and the energy loss due to light scattering of the beam can be measured and recorded. Bacteria, as is known, upon growth or reproduction scatters light and as bacteria in the sample reproduce or proliferate such as in response to cultivation, more light is scattered thereby further increasing the optical density of the sample and hence at the end of the time interval the transilluminating beam or ray can again be passed through the sample and the increased energy loss caused by increased optical density or light scattering can again be measured and compared vis-a-vis the earlier measurement. The difference in energy level of the light beam can be used, empirically, and particularly knowing the production rate of the bacteria present, to provide a measurement of bacteria growth in the sample over the time interval. It will be further understood that circuitry embodied in the monolithic chip 132 and the photoemitter and photodetector pairs E1-D1 and E2-D2, in combination with the collimating and collecting lens and reflectors of the transparent cuvette 110 function as a photometer or turbidity meter.

Referring now specifically to the operation of the present invention when used in a urinary tract infection kit, it will be presumed that a urine sample has been taken from a urinary tract suspected of having a urinary tract infection, that the urine sample has been diluted in a suitable liquid culture growth medium, such as eugonic broth, to seed the broth, that the cap 150 of the assembly 100 has been removed, and that the seeded liquid culture growth medium has been poured into the receptacle 200 where it flows through the two funnels 201, 202 where it substantially divides and enters into the cells 111 and 112 of the transparent cuvette 110. It will be understood that cell 111 has been preconditioned to grow only Gram positive bacteria by having a Gram negative inhibitor placed therein such as by coating the walls of cell 111 with sodium azide powder which, as known to those skilled in the art, inhibits the growth of virtually all Gram negative bacteria. However, cell 112 has not been preconditioned and hence both Gram negative and Gram positive bacteria will grow in cell 112. The cap 150 will then be placed into the receptacle 200 with the arrows 119 and 159 aligned to initiate operation of the assembly by energization of the electrical circuit 130 as taught above. It will be understood that the monolithic chip 132 of the electrical circuitry 130, FIG. 10, may have a suitable circuit embodied therein to cause all of the photoemitters E3, E4 and E5 to be temporarily activated, or activated in a predetermined sequence, to provide indication to the user that the self-sufficient incubation assembly is functioning; thereafter such photoemitters will be extinguished and bacteria cultivation commenced and continued for a time interval.

Figure 9:
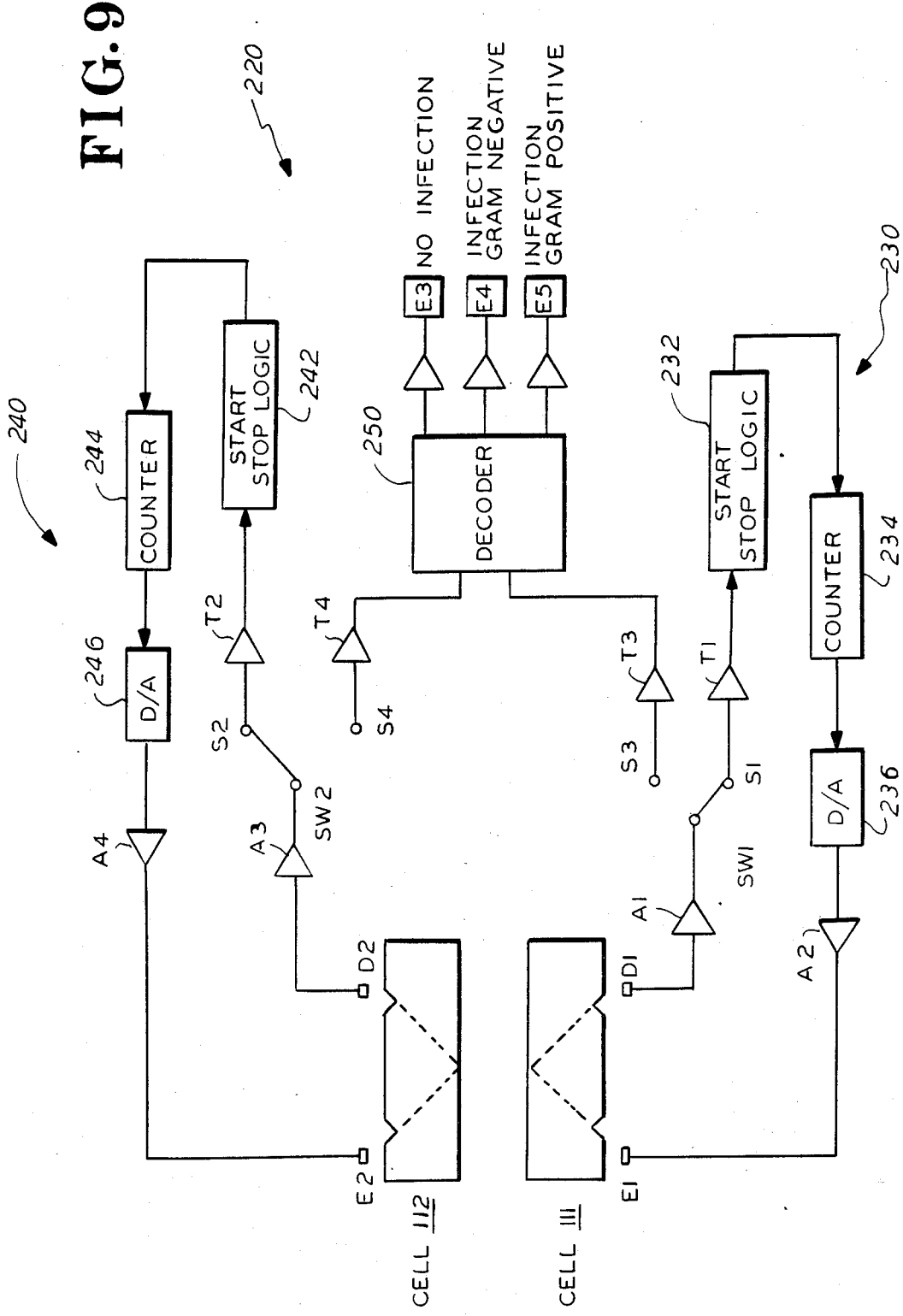
FIG. 9 is a diagrammatical illustration of baselining circuitry.
Figure 16:
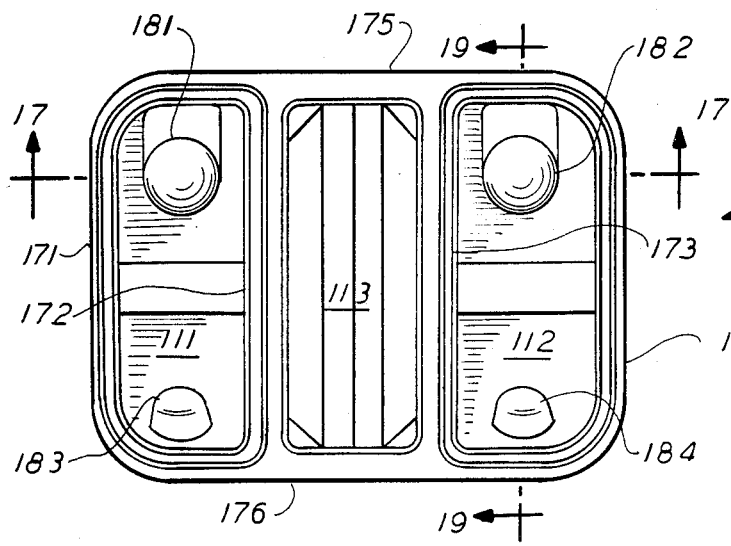
FIG. 16 is a plan view of the bottom of the transparent cuvette.

As is further known to those skilled in the art, to provide significant turbidity measurements at the beginning and end of the time interval, the photometer or turbidity meter must be baselined to provide appropriate measurement references against which future measurements may be measured or compared for significant results. Accordingly, the electrical circuitry may be suitably baselined for significant measurements. Referring to FIG. 9, there is shown such baselining circuitry, indicated by general numerical designation 220, which may be used for such baselining, although illustrated as a block diagram in FIG. 9, it may be embodied in the monolithic chip 132 of FIG. 10 in a manner known to those skilled in the art. The baselining circuitry 220 is a dual channel circuit including channel 230 associated with cuvette cell 111 and channel 240 associated with cuvette cell 112. Channel 230 includes the series connection of the photoemitter E1, photodetector D2, amplifier A1, switching network S1, threshold comparator T1, start-stop logic 232, counter 234, digital to analog converter 236 and amplifier A2; similarly, the channel 240 includes the series connected components as shown. Additionally, the baselining circuit includes the threshold comparators T3 and T4 connected to the decoder 250 which in turn is provided with three outputs as shown, for providing one of three binary outputs indicative of the bacterial conditions shown, namely no infection, Gram negative infection, or Gram positive infection.

Continuing from above, it will again be presumed that the circuitry 130 has been energized by the battery 144 due to the closure of the cap 150 and now the operation of the baselining circuitry 220 and the decoder 250 for providing the bacterial infection indication shown will be described. With regard to baselining channel 230, upon energization the switching network SW1 assumes state S1 whereupon photoemitter E1 has no output and hence photodetector D1 has no input and therefore no output; this lack of output will be reflected to amplifier A1 and threshold comparator T1 will signal the start-stop logic 232 to initiate counting which is then converted, digital to analog by the converter 236, boosted by amplifier A2, and reflected in a gradually increasing light level emanating from the photoemitter E1. At such time the evoked response of the photodetector D1 reaches the preset level of threshold detector T1, the start-stop logic is signalled to stop counting thus freezing the output level of the photoemitter E1 and channel 230 is now baselined; similarly, channel 240 is also baselined to the preset level of the threshold detector T2. At the conclusion of the cultivation time interval, for example approximately four hours, which time elapse is built into the circuitry of the monolithic chip 132 in a manner known to those skilled in the art, the switching network SW1 assumes state S2 and the evoked response of the photodetector D1 in response to the output of the photoemitter E1 transilluminating the cuvette cell 111 is connected through amplifier A1 to threshold comparator T3 and compared with its preset threshold level and if the later evoked response of the photodetector D1 falls below the threshold of comparator T3 a binary 0 signal is transmitted to the decoder 150 to indicate the absence of clinically significant Gram positive bacteria growth in cell 111. However, if the evoked response of the photodetector D1 is at least equal to or greater than the preset threshold of threshold comparator D3, a binary 1 signal is transmitted to the decoder 250 to indicate the presence of clinically significant Gram positive bacteria growth in cell 111. Similarly, threshold comparator T4 is preset to send a binary 0 or 1 signal to the decoder 250 to respectively indicate the absence of clinically significant levels of Gram negative and/or Gram positive bacteria growth in cell 112 or the presence of clinically significant levels of Gram negative and/or Gram positive bacterial growth in cell 112. It will be understood that the preset threshold levels of the respective threshold comparators will be preset empirically and in accordance with the recognized respective reproduction and growth rates of Gram positive and Gram negative bacteria, for example the preset threshold of threshold comparator T4 of channel 240 will be approximately twice the preset level of threshold comparator T3 of channel 230 since it is known that Gram negative bacteria grow at approximately twice the rate of Gram positive bacteria. The decoder 250 will interpret or decode the binary 1 or 0 signals received from the respective threshold comparators T3 and T4 to provide an indication of bacterial growth in accordance with the algorithm, sometimes referred to in the art as a truth-table, set forth in FIG. 11. It will be further understood that the algorithm or truth-table of FIG. 11 will also be embodied in suitable circuitry included in the monolithic chip 132 of the electrical circuit 130.

Figure 17:
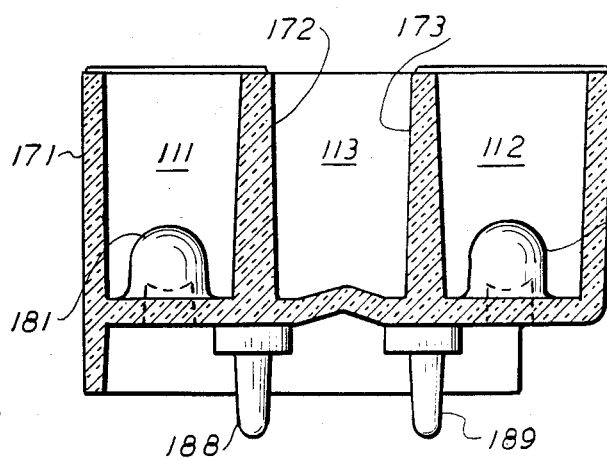
FIG. 17 is a cross-sectional view taken along the line 17—17 of FIG. 16.
Figure 19:
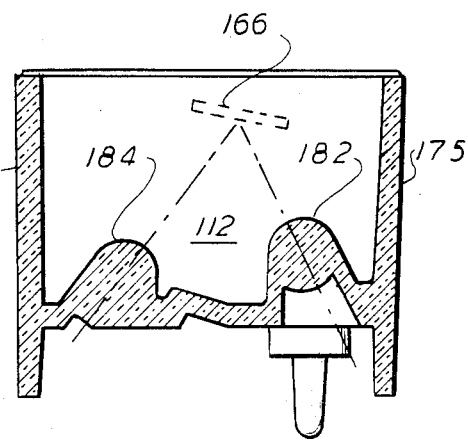
FIG. 19 is a cross-sectional view taken along the line 19—19 of FIG. 16.
Figure 18:
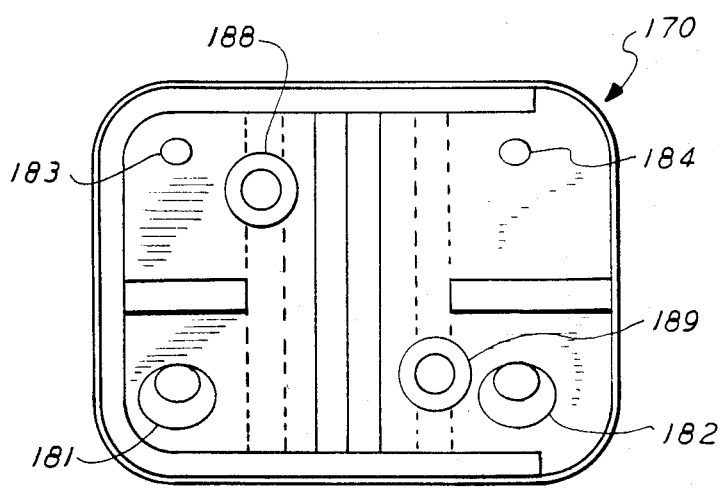
FIG. 18 is a bottom view of the transparent cuvette bottom of FIG. 16.

Referring now to the decoder algorithm of FIG. 11, upon the decoder 250 of FIG. 9 receiving the binary 1 from the output of cell 111 and a binary 0 from the output of cell 112, this will be interpreted and the appropriate photoemitter E4 illuminated to indicate the presence of clinically significant levels of Gram positive bacteria in the urine sample. Upon the decoder receiving a binary 0 from cell 11 and a binary 1 from cell 112, this will be interpreted by the decoder 250 to indicate the presence of clinically significant levels of Gram negative bacterial and photoemitter E4 will be illuminated to provide such indication. Should a binary 0 be received from both cells, this will be decoded to indicate the absence of any clinically significant infection and photoemitter E3 wil be illuminated to provide such visual indication. However, it is possible for the decoder to receive a binary 1 from both cell 111 and cell 112 and, as indicated in FIG. 17, this is interpreted or decoded by the decoder 250 to indicate the presence of clinically significant levels of Gram positive bacteria. This results from one or two possible situations and the following logic: one possibility is that Gram positive bacteria were present in such large quantity or experienced such large growth during cultivation as to exceed both the preset threshold level of threshold comparator T3 of the Gram positive cell 111 and the preset threshold level of the threshold comparator T4 of the Gram positive and/or Gram negative bacteria cell 112, the other possibility is that there were mixed bacteria present, indicating the possibility of a mixed infection, and that the growth of the gram positive bacteria in cell 112 exceeded the threshold of threshold comparator T3 and that there was either mixed or Gram negative bacteria growth in cell 112 sufficient to exceed the preset threshold of threshold comparator T4. In such event, as known to those skilled in the art, treatment for Gram positive bacteria or Gram positive infection is indicated.

It will be noted from FIGS. 2, 4, and 5, and from FIG. 10 where cuvette 110, cell 111 and cell 112 are shown in dashed outline, that the electrical circuitry 130 and the temperature control element 135 are in intimate physical contact with the cuvette 110 specifically the underside thereof. Hence, the temperature of the temperature control element 135 will be substantially the same as the temperature of the cuvette and the seeded culture growth medium contained therein whereby improved temperature control of the medium is provided, and the heat of operation of the electrical circuitry 130 will supplement the heat applied by the heating resistor 133 and battery 144 to the cuvette 110 and the seeded culture growth medium received therein whereby the energy required to be supplied by the battery 144 will be less than would be required were the electrical circuitry 130 to be located externally of the cuvette and not in intimate physical contact therewith.

Referring again to FIG. 10, it will be understood that the photoemitter E1 of FIG. 10 and photoemitter 232 of FIG. 20 are positioned at the proper point along the optical axis of the respective collimating lens 181 of the cuvette 110 and collecting lens 212 of cuvette 210 to maximize collimation of the light emitted by the photodetector for transilluminating the culture growth medium received by the respective cuvette 110 and 210 and the photodetector D1 of FIG. 10 and the photodetector 233 of FIG. 20 are positioned along the optical axis of the respective collecting lens 183 and 214 to maximize the collection of the light transilluminating the culture growth medium and exiting the respective cuvette 110 or 210 for photometric measurement.

It will be further understood by those skilled in the art that many modifications and variations of the present invention may be made without departing from the spirit and the scope thereof.

What is claimed is:

1. A molded cuvette with molded optical elements for use in photometric measurements, comprising:

molded transparent means providing a cell for receiving fluid undergoing change in optical characteristics which change modifies the energy level of a transluminating ray entering said transparent means, passing through and transluminating said fluid, and exiting said transparent means;

said molded transparent means provided with molded collimating lens for collimating said transluminating ray upon entering said transparent means and provided with molded collecting lens for collecting said transluminating ray upon passing through said fluid and exiting said transparent means; and at least a portion of said molded transparent means and said molded collimating and said molded collecting lens molded together as a single unit.

2. A cuvette according to claim 1 wherein said molded transparent means are further provided with molded entrance means for admitting said fluid into said cell and with molded venting means for venting said cell upon entry of said fluid into said cell.

3. A cuvette according to claim 1 wherein said cuvette includes reflecting means and wherein said molded collimating lens and molded collecting lens each has an axis, said reflecting means and said collimating lens and said collecting lens mutually disposed such that said transluminating ray is collimated along the axis of said collimating lens and is reflected by said reflecting means along the axis of said collecting lens.

4. A cuvette according to claim 1 wherein said molded collimating lens and said molded collecting lens are each meniscus lens.

5. A cuvette according to claim 2 wherein said molded transparent means comprise top and bottom molded members, wherein said top member is provided with reflecting means, wherein said collimating lens and said collecting lens are each meniscus lens with each lens molded together with said bottom member into a single unit and extending inwardly into said cell and disposed at a respective predetermined angle with respect to said reflecting means, and wherein said entrance and venting means are separate means with each comprising a tubular member molded together with said top member into a single unit and extending upwardly therefrom.

6. A molded cuvette with molded optical elements for use in photometric measurements, comprising:

molded transparent means providing a plurality of adjacent cells, each cell for receiving a fluid undergoing change in optical characteristics which change modifies the energy level of a transluminating ray entering said transparent means, passing through said fluid, and exiting said transparent means;

said molded transparent means provided with a plurality of pairs of molded collimating lens and molded collecting lens with each pair associated with one of said cells, said collimating lens of each pair for collimating a transluminating ray passing through said transparent means and entering one of said cells and said collecting lens of said pair for collecting said transluminating ray passing through fluid received in said one of said cells and exiting said transparent means; and at least a portion of said molded transparent means and said molded collimating and molded collecting lens molded together as a single unit.

7. A cuvette with molded optical elements according to claim 6 further including a plurality of pairs of molded entrance means and molded venting means with each pair associated with one of said cells, said entrance means of each pair for admitting fluid into one of said cells and said venting means of said pair for venting said one of said cells upon entry of fluid into said one of said cells.

8. A cuvette according to claim 6 wherein said molded transparent means includes a plurality of surfaces each for receiving a reflector associated with one of said cells, and wherein said molded collimating lens and said molded collecting lens of each pair is each disposed at a respective predetermined angle with respect to the reflector associated with the cell with which said pair of lens is associated.

9. A cuvette with molded optical elements according to claim 6 wherein each of said molded collimating lens and each of said molded collecting lens is a meniscus lens.

10. A cuvette with molded optical elements according to claim 7 wherein said molded transparent means comprise molded top and bottom members, wherein said molded top member is provided with a plurality of reflecting means each associated with one of said cells, wherein said molded collimating lens and said molded collecting lens are each meniscus lens and wherein said collimating lens and collecting lens of each pair are molded together with said bottom member into a single unit with each lens disposed at a respective predetermined angle with respect to the reflecting means associated with the cell with which said pair of lens are associated, and wherein said molded entrance means and said molded venting means are each tubular means and wherein said entrance means and said venting means of each pair are molded together with said top member into a single unit and extending upwardly therefrom.

11. A cuvette with molded optical elements according to claim 10 wherein said bottom member is provided with molded light trap means intermediate adjacent cells, and said light trap means for preventing a transluminating ray illuminating one of said cells from also transluminating an adjacent cell.

12. A cuvette with molded optical elements for use in photometric measurements, comprising:
   molded means for receiving a medium undergoing change in optical characteristics which change modifies the energy level of a transluminating ray passing through and transluminating said medium;
   said molded means provided with molded collimating lens and molded collecting lens, said collimating lens for receiving and collimating said transluminating ray and transmitting said ray into said medium and said collecting lens for receiving and collecting said transluminating ray upon passing through said medium and transmitting said transluminating ray from said cuvette; and
   at least a portion of said molded means and said molded collimating lens and said molded collecting lens molded together as a single unit.

13. A cuvette according to claim 12 wherein said collimating lens and said collecting lens each has an axis and wherein said axes are disposed in a predetermined relationship with respect to each other.

14. A cuvette according to claim 13 wherein said collimating lens and said collecting are each meniscus lens.

15. A molded cuvette with molded optical means for use in photometric measurements, comprising:
   molded means for receiving a medium undergoing change in optical characteristics which change modifies the energy level of a ray of energy passing through said medium;
   said means provided with first molded and second molded ray modifying optical means, said first molded ray modifying optical means for receiving and modifying said ray in a first predetermined manner and for transmitting said ray into said medium and said second molded ray modifying optical means for receiving and modifying said ray in a second predetermined manner upon passing through said medium and for transmitting said ray from said cuvette;
   at least a portion of said molded means and said molded collimating lens and said molded collecting lens molded together in a single unit.

* * * * *

UNITED STATES PATENT AND TRADEMARK OFFICE
CERTIFICATE OF CORRECTION

PATENT NO. : 4,577,970
DATED : March 25, 1986
INVENTOR(S) : Peter M. Meserol

It is certified that error appears in the above-identified patent and that said Letters Patent are hereby corrected as shown below:

Claim 15, Column 12, line 38, before "molded" (first occurrence insert --first--; same line delete "collimating lens"; same line, after "said" insert --second--; same line, delete "collecting";

Claim 15, Column 12, line 39, delete "lens" and insert instead --ray modifying optical means--.

Signed and Sealed this

Twenty-third Day of August, 1988

Attest:

DONALD J. QUIGG

Attesting Officer        Commissioner of Patents and Trademarks